(12) United States Patent
Benje

(10) Patent No.: US 9,981,890 B2
(45) Date of Patent: May 29, 2018

(54) METHOD AND A DEVICE FOR SYNTHESIZING 1.2-DICHLOROETHANE

(71) Applicants: Thyssenkrupp Industrial Solutions AG, Essen (DE); Thyssenkrupp AG, Essen (DE); Vinnolit GmbH & Co. KG, Burgkirchen (DE)

(72) Inventor: Michael Benje, Bad Soden (DE)

(73) Assignees: Thyssenkrupp Industrial Solutions AG, Essen (DE); Thyssenkrupp AG, Essen (DE); Vinnolit GmbH & Co. KG, Burgkirchen (DE)

( * ) Notice: Subject to any disclaimer, the term of this patent is extended or adjusted under 35 U.S.C. 154(b) by 0 days. days.

(21) Appl. No.: 15/329,992

(22) PCT Filed: Jul. 27, 2015

(86) PCT No.: PCT/EP2015/067181
§ 371 (c)(1),
(2) Date: Jan. 27, 2017

(87) PCT Pub. No.: WO2016/016200
PCT Pub. Date: Feb. 4, 2016

(65) Prior Publication Data
US 2017/0267610 A1  Sep. 21, 2017

(30) Foreign Application Priority Data

Jul. 29, 2014 (DE) .................. 10 2014 214 872

(51) Int. Cl.
*C07C 17/02* (2006.01)
*B01J 19/24* (2006.01)

(52) U.S. Cl.
CPC ............... *C07C 17/02* (2013.01); *B01J 19/24* (2013.01); *B01J 2219/24* (2013.01)

(58) Field of Classification Search
CPC .............................. C07C 17/02; C07C 19/045
See application file for complete search history.

(56) References Cited

U.S. PATENT DOCUMENTS 2,099,231 A  11/1937  Ruys et al.
2,245,776 A   6/1941  Groll et al.
(Continued)

FOREIGN PATENT DOCUMENTS

DE     529524    7/1931
DE    4103281    8/1992
(Continued)

*Primary Examiner* — Jafar Parsa
(74) *Attorney, Agent, or Firm* — Rudy J. Ng; Bozicevic, Field & Francis LLP

(57) ABSTRACT

The invention relates to a method for synthesizing 1.2-dichloroethane from ethylene and chlorine via low temperature direct chlorination of ethylene in the presence of a catalyst under conditions in which the synthesized 1.2-dichloroethane is condensed out, however, the ethylene and the chlorine are gaseous, in a reactor (3), wherein the stoichiometric ratio of ethylene to chlorine is adjusted in the reactor (3) such that there is an excess of ethylene. The invention further relates to a device for synthesizing 1.2-dichloroethane from ethylene and chlorine via low temperature direct chlorination of ethylene in the presence of a catalyst under conditions in which the synthesized 1.2-dichloroethane is condensed out, however, the ethylene and the chlorine are gaseous, in a reactor (3), wherein the stoichiometric ratio of ethylene to chlorine is adjustable in the reactor (3) such that there is an excess of ethylene.

20 Claims, 3 Drawing Sheets

(56) References Cited

U.S. PATENT DOCUMENTS

| | | | |
|---|---|---|---|
| 3,941,568 A | 5/1976 | Kurtz et al. | |
| 4,410,747 A * | 10/1983 | Akiyama | C07C 17/02 570/247 |
| 6,841,708 B1 | 1/2005 | Benje | |
| 2010/0036180 A1 * | 2/2010 | Leduc | C07C 17/02 570/220 |

FOREIGN PATENT DOCUMENTS

| | | |
|---|---|---|
| DE | 4318609 | 7/1994 |
| DE | 19641562 | 1/1998 |
| EP | 2196446 | 6/2010 |
| JP | 2006335665 | 12/2006 |
| KR | 20120067400 | 6/2012 |
| RU | 2051891 | 1/1996 |

* cited by examiner

METHOD AND A DEVICE FOR SYNTHESIZING 1.2-DICHLOROETHANE

CROSS-REFERENCE TO RELATED APPLICATIONS

This application is the U.S. national phase under 35 U.S.C. § 371 of PCT International Application No. PCT/EP2015/067181, which has an international filing date of Jul. 27, 2015 and designated the United States of America, which application claims benefit of priority to DE Application No. 10 2014 214 872.3, filed Jul. 29, 2014, the disclosures of each of which are incorporated by reference herein.

TECHNICAL FIELD OF THE INVENTION

The present invention relates to a method and device for synthesizing 1,2-dichloroethane from ethylene and chlorine by low temperature direct chlorination of ethylene in the presence of a catalyst.

PRIOR ART

These types of methods for synthesizing 1,2-dichloroethane (also known as ethylene dichloride or for short EDC/DCE) are typically employed in the production of vinyl chloride (also known as VC or VCM). Vinyl chloride is an intermediate product obtained in the production of polyvinyl chloride (PVC). 1,2-Dichloroethane is generally synthesized from ethylene and chlorine by the so-called direct chlorination of ethylene. The 1,2-dichloroethane obtained can then be converted into vinyl chloride by pyrolysis to eliminate hydrogen chloride (HCl).

Commercially practiced processes for direct chlorination of ethylene typically use the reaction product EDC also as reaction medium. The reactants chlorine and ethylene are introduced in gaseous form into liquid EDC, where they dissolve and then react with each other. The reactants are in effect admixed to a circulating stream of EDC because the reaction medium is moving under natural circulation or under forced circulation. In the case of natural circulation reactors, the reactants are typically admixed in the riser pipe of the reactor.

The catalyst used is generally a Lewis acid. This is often iron(III) chloride (FeCl3) for cost reasons. More sophisticated catalyst systems additionally include, for example, an alkali metal halide, usually sodium chloride (NaCl), as well as the Lewis acid. Catalyst systems of this type are capable of preventing unwanted secondary reactions such as the continued chlorination of EDC into 1,1,2-trichloroethane even at comparatively high temperatures and therefore offer a commercial advantage over the use of iron(III) chloride. A catalyst system of this type is described in DE 43 18 609 for example.

Prior art methods differ with regard to reaction temperature and reaction management. In a so-called low temperature direct chlorination (LTDC), the reactor is operated at below the boiling point of the EDC reaction medium, which (at atmospheric pressure) is 84° C. The product of the LTDC process is withdrawn from the reactor in liquid form. Methods of this type are operated with excess chlorine, under which conditions the iron chloride catalyst may be formed by reaction of chlorine with iron from the reactor wall or from dedicated internals such as packing elements etc. Since the liquid reaction product still contains dissolved chlorine as well as catalyst, it first has to be treated with one or more washing steps involving water and/or aqueous sodium hydroxide solution. This generates a wastewater stream which has to be treated in turn. A distillative workup of the product likewise necessitates an additional distilling step to remove dissolved water.

A high temperature direct chlorination (HTDC) is carried out at above the boiling point of the reaction medium. As a result, the reaction product is withdrawable from the reactor in vapor form, leaving the catalyst behind in the reactor. This not only makes the use of advanced catalyst systems a possibility but also allows optimization of catalyst concentration.

The above-described direct chlorination plants operating according to the low temperature direct chlorination process require the removal of excess chlorine and/or chlorinated by-products from the 1,2-dichloroethane. In addition, excess chlorine leads to increased corrosion in the reactor, shortening reactor life.

DISCLOSURE OF THE INVENTION

The problem addressed by the present invention is that of specifying a method and device for synthesizing 1,2-dichloroethane from ethylene and chlorine by low temperature direct chlorination of ethylene whilst reducing the purification requirements of the synthesized 1,2-dichloroethane and extending reactor life.

The problem is solved by a method for synthesizing 1,2-dichloroethane from ethylene and chlorine by low temperature direct chlorination of ethylene in the presence of a catalyst in a reactor under conditions where the synthesized 1,2-dichloroethane condenses out while the ethylene and the chlorine are gaseous, which method comprises the step of adjusting the stoichiometric ratio of ethylene to chlorine in the reactor such that ethylene is present in excess.

The problem is further solved by a device for synthesizing 1,2-dichloroethane from ethylene and chlorine by low temperature direct chlorination of ethylene in the presence of a catalyst in a reactor under conditions where the synthesized 1,2-dichloroethane condenses out while the ethylene and the chlorine are gaseous, wherein the stoichiometric ratio of ethylene to chlorine in the reactor is adjustable such that ethylene is present in excess.

In the method and device, the reaction in the reactor is operated in excess ethylene, so the chlorine introduced into the reactor is essentially consumed to synthesize 1,2-dichloroethane. The formation of more highly chlorinated by-products in addition to 1,2-dichloroethane is reduced. There is accordingly no need to remove chlorine from the synthesized 1,2-dichloroethane and the purification requirements of 1,2-dichloroethane to remove more highly chlorinated by-products decrease. In addition, the reduced chlorine content as compared with the prior art leads to reduced corrosion in the reactor, substantially extending reactor life.

The method of the present invention is useful both to build new low temperature direct chlorination devices and to revamp existing low temperature direct chlorination devices.

The conditions in the reactor are chosen such that the synthesized 1,2-dichloroethane condenses out while the ethylene and the chlorine are by contrast gaseous. The temperature in the reactor is preferably set to below the boiling point of 1,2-dichloroethane, particularly to below 84° C.

In an advantageous form of the method, the stoichiometric ratio of ethylene to chlorine is not less than 1.01:1. The stoichiometric ratio of ethylene to chlorine is preferably not less than 1.05:1 and more preferably not less than 1.10:1.

Advantageously, the stoichiometric ratio of ethylene to chlorine in the reactor is monitored and the feed of ethylene and chlorine to the reactor is closed loop controlled such that ethylene is present in excess. Monitoring may be effected continuously or at discrete points in time. The reactor preferably includes a detection device for detecting the stoichiometric ratio. The reactor closed loop control may be effected via a control means connected to the detection device and via which the flow of ethylene and/or chlorine in the reactor is adjusted.

In an advantageous embodiment of the method according to the present invention, the reactor has withdrawn from it a 1,2-dichloroethane liquid stream which is partly vaporized in a vaporizing device. The 1,2-dichloroethane withdrawn from the reactor is partly converted by the vaporizing device into gaseous 1,2-dichloroethane, which has a high degree of purity. This has the advantage that the 1,2-dichloroethane stream withdrawn from the reactor is purified of the catalyst. Preference is given to employing a single-stage vaporizing device, reducing cost and inconvenience as compared with a multi-step vaporization process.

In a particularly advantageous embodiment, less than 50% of the 1,2-dichloroethane stream removed from the reactor is vaporized in the vaporizing device. Preferably, the proportion to which the 1,2-dichloroethane stream removed from the reactor is vaporized in the vaporizing device corresponds to the 1,2-dichloroethane quantity produced in said reactor.

A preferred embodiment provides that the vaporizing device is configured as a falling stream evaporator. The 1,2-dichloroethane stream is preferably supplied to the falling stream evaporator from above. The 1,2-dichloroethane may flow downwardly in the falling stream evaporator and partly vaporize in the falling stream evaporator as a result of heating. The nonvaporized proportion of the 1,2-dichloroethane stream removed from the reactor may collect in the bottom region of the falling stream evaporator.

Preferably, the nonvaporized proportion of the 1,2-dichloroethane stream withdrawn from the reactor is returned into the reactor, so the catalyst contained in the nonvaporized stream of 1,2-dichloroethane may be reused in the reactor.

It will further be found to be advantageous for the vaporizing device to be heated using the condensation heat from the vapor of a distillation column, and/or the vaporizing device to be heated using the reaction heat from a plant for high temperature direct chlorination of ethylene. This has the advantage that the heat required for vaporization is provided from heat recovery measures, so no additional energy need be supplied. The distillation column is preferably a distillation column for separating higher boiling components from 1,2-dichloroethane. The distillation column is preferably operated at an overhead temperature in the range from 120° C. to 150° C., more preferably at an overhead temperature in the range from 127° C. to 135° C. Heating with the condensation heat of the vapor of the distillation column is preferably employed when the upgrade of an existing LTDC plant does not entail an increased capacity. To heat the vaporizing device with the reaction heat from a plant for high temperature direct chlorination of ethylene, a vaporous stream of 1,2-dichloroethane may be condensed and/or a liquid stream of 1,2-dichloroethane may be cooled down.

In a further advantageous embodiment, before being fed to the vaporizing device, the 1,2-dichloroethane stream removed from the reactor is preheated using, preferably warm, a 1,2-dichloroethane stream withdrawn from the vaporizing device and/or using a specifically liquid, preferably warm, 1,2-dichloroethane stream from a plant for high temperature direct chlorination of ethylene. This makes it possible to cool down the 1,2-dichloroethane stream withdrawn from the vaporizing device to recover the energy released in the process. It is particularly advantageous for the heat exchange between the streams withdrawn from the vaporizing device and the reactor to be effected crosscurrently. To cool down the 1,2-dichloroethane stream withdrawn from the vaporizing device, a device for flash evaporation is a useful alternative.

An advantageous embodiment provides that the vaporous 1,2-dichloroethane stream emerging from the vaporizing device is fed into a distillation column. Preferably, the distillation column is used to separate off compounds having a higher boiling point than 1,2-dichloroethane. This embodiment is preferentially employed when as part of the upgrade of an existing LTDC plant, the production capacity is to be increased at the same time by building a new HTDC plant as an annexe.

The catalyst used in the method of the present invention preferably comprises iron(III) chloride (FeCl3) and/or sodium chloride (NaCl).

Advantageously, an ethylene-containing off-gas from a high temperature direct chlorination reactor is fed to the reactor, so this off-gas is usable for low temperature direct chlorination, while the ethylene content is used for production of 1,2-dichloroethane. The ethylene-containing off-gas is preferably compressed in a gas jet gas compressor, more particularly operated using a gaseous stream of ethylene.

The advantageous features described above in connection with the method of the present invention may also find application, alone or combined, in the device of the present invention.

Further details, features and advantages of the invention will be apparent from the drawings as well as the subsequent description of preferred embodiments by means of the drawings. These drawings illustrate merely exemplary embodiments of the invention, which do not limit the concept of the invention.

SHORT DESCRIPTION OF FIGURES

EMBODIMENTS OF THE INVENTION

In the various figures, like reference signs are provided for like parts and these are therefore each generally only identified/mentioned once.

Figure 1:
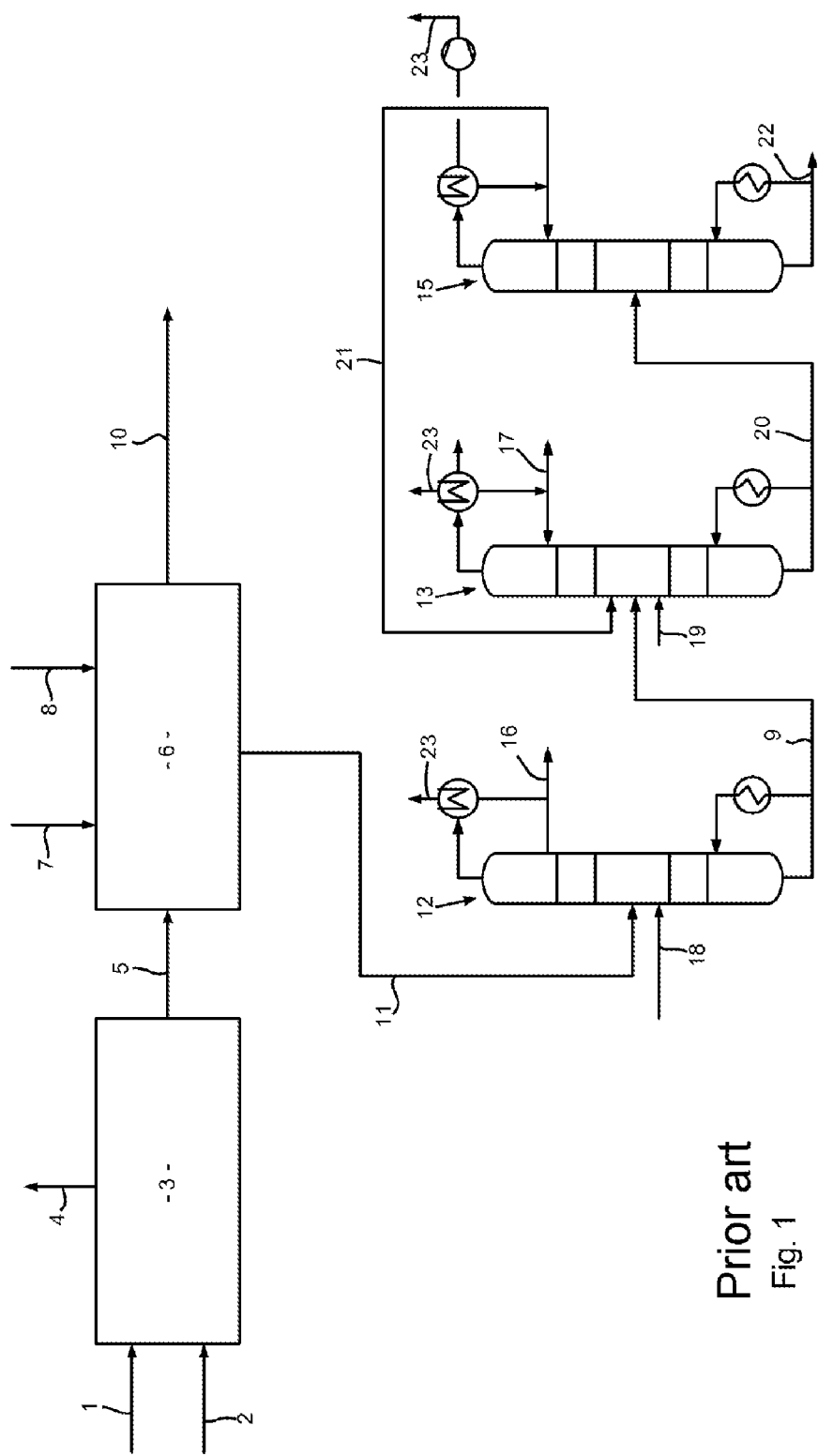
FIG. 1 shows in a schematic depiction a device for synthesizing 1,2-dichloroethane from ethylene and chlorine by low temperature direct chlorination of ethylene as per the prior art.

FIG. 1 depicts a prior art device for synthesizing 1,2-dichloroethane from ethylene and chlorine by low temperature direction chlorination of ethylene (an LTDC plant). Ethylene 1 and chlorine 2 are fed under the conditions of excess chlorine into an LTDC reactor 3, where they are dissolved in EDC and react with each other to form EDC. The reactor off-gas 4 is withdrawable at the top of the reactor. The reaction proceeds at a temperature below the boiling point of EDC. The produced, catalyst-containing EDC 5 is withdrawn from the reactor in liquid form and subjected to a wash with water 7 and aqueous sodium hydroxide solution 8, in the course of which the catalyst transfers into the aqueous phase and any chlorine still present is converted by reaction with aqueous sodium hydroxide solution into sodium hypochlorite, which likewise dissolves in the aqueous phase. The wastewater stream 10 has to be sent to a further treatment.

The now moist EDC 11 is fed into a dewatering column 12, where, in an integrated system with a plant for production of VCM, likewise still moist EDC 18 from an oxychlorination plant may be worked up and at the top of which water and low boilers 16 are separated off.

The dried EDC 9 is fed into a high boilers column 13, at the top of which the purified product EDC 17 is withdrawn. At the bottom end of the high boilers column, a concentrated solution of high boilers in EDC 20 is withdrawn and fed into a vacuum column 15. In this column, high boilers 22 are separated off at the bottom end while the EDC 21 generated at the top is returned to the high boilers column 13. Where there is a complete plant complex for production of VCM, a backstream 19 of EDC from a plant for thermal cracking of EDC is additionally worked up in the high boilers column.

The depiction of the three-stage distillative workup of EDC via columns 12, 13 and 15 is exemplary—this manner of working up is known to a person skilled in the art and does not form part of the invention. To clarify the incorporation in a plant complex for production of vinyl chloride, reference is made to EDC streams from an oxychlorination plant 18 and from a plant for thermal cracking of EDC 19. These interrelationships are also known to a person skilled in the art.

Figure 2:
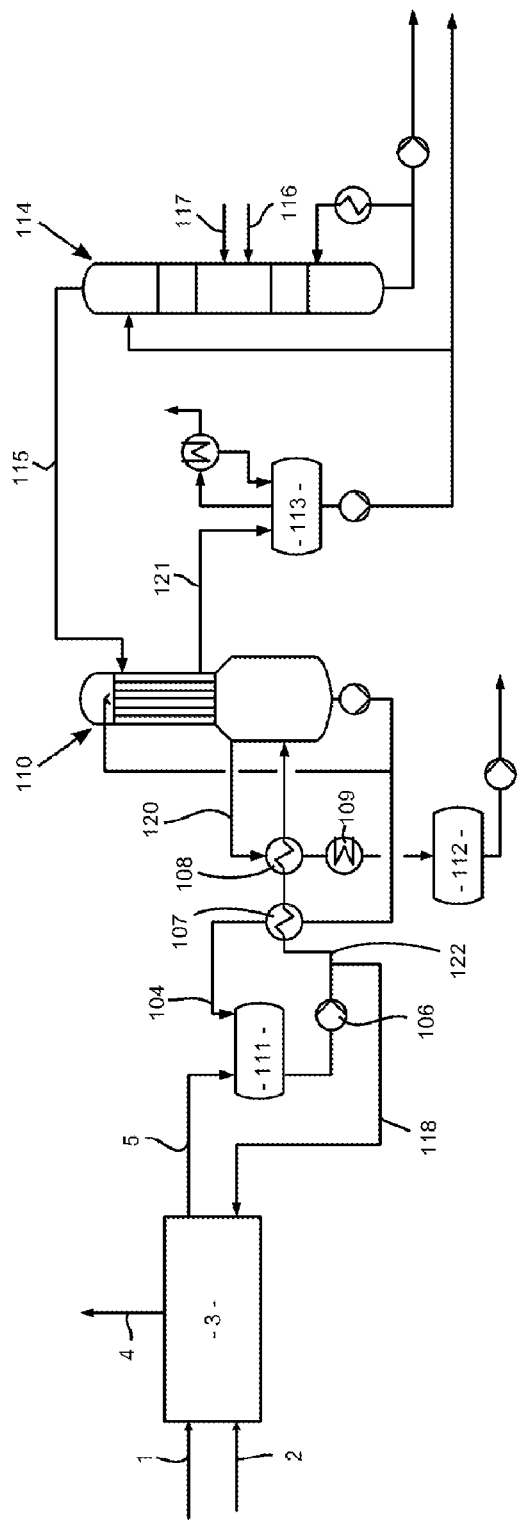
FIG. 2 shows in a schematic depiction a first exemplary embodiment of a device as provided by the invention for synthesizing 1,2-dichloroethane from ethylene and chlorine.

FIG. 2 depicts a first exemplary embodiment of a device for synthesizing 1,2-dichloroethane according to the invention. In this exemplary embodiment, the vaporizing device is heated with the vapor of a distillation column.

FIG. 2 shows an LTDC plant whose reaction product is vaporized in a single-stage vaporizing step wherein the heat required for vaporization is supplied as the latent heat of the vapor stream of a high boilers column. No additional steam is consumed in the process. Ethylene 1 and chlorine 2 are fed into an LTDC reactor 3, where they react to form EDC. The reactor off-gas stream 4 is withdrawable at the top of the reactor. The LTDC reactor has withdrawn from it a liquid, catalyst-containing EDC stream 5, which is passed into a receiver 111. In a preferred embodiment, the EDC stream 5 is greater than the EDC quantity produced in the reactor. A pump 106 passes the EDC stream through one or more heat exchangers 107, 108, which are used for preheating, and it is preheated with the bottoms stream 104 from the vaporizing apparatus 110 and/or with the vaporous product EDC 120 from the vaporizing apparatus 110. After preheating, the EDC stream enters the vaporizing apparatus 110, where an EDC quantity corresponding to the EDC quantity produced in the LTDC reactor 3 is vaporized. The vaporized EDC stream 120 is cooled down in the preheater 108 and in a further heat exchanger 109, collected in the product receiver 112 and pumped to the plant limits or to a downstream part of the integrated plant for VCM production. The nonvaporized, catalyst-containing EDC fraction 104 from the vaporizing apparatus 110 is pumped back into the receiver 111, after being cooled down by heat exchange in the preheater 107. From the receiver 111, an EDC stream corresponding to the nonvaporized EDC fraction is pumped back into the LTDC reactor.

The vaporizing apparatus 110 serves as overhead condenser to the distillation column, which is configured as a high boilers column 114 and which may also be used to work up further streams from the integrated plant for VCM production such as back EDC from the thermal EDC cracker 116 or EDC from an oxychlorination 117 and dried in a dewatering column. The condensed EDC 121 is collected in the return stream container 113 of the high boilers column 114 and pumped as return stream to the column 114 and/or as product to the plant limits.

The method described in the first exemplary embodiment is particularly useful for upgrading existing LTDC plants where the capacity is not to be simultaneously increased as part of the upgrade.

Figure 3:
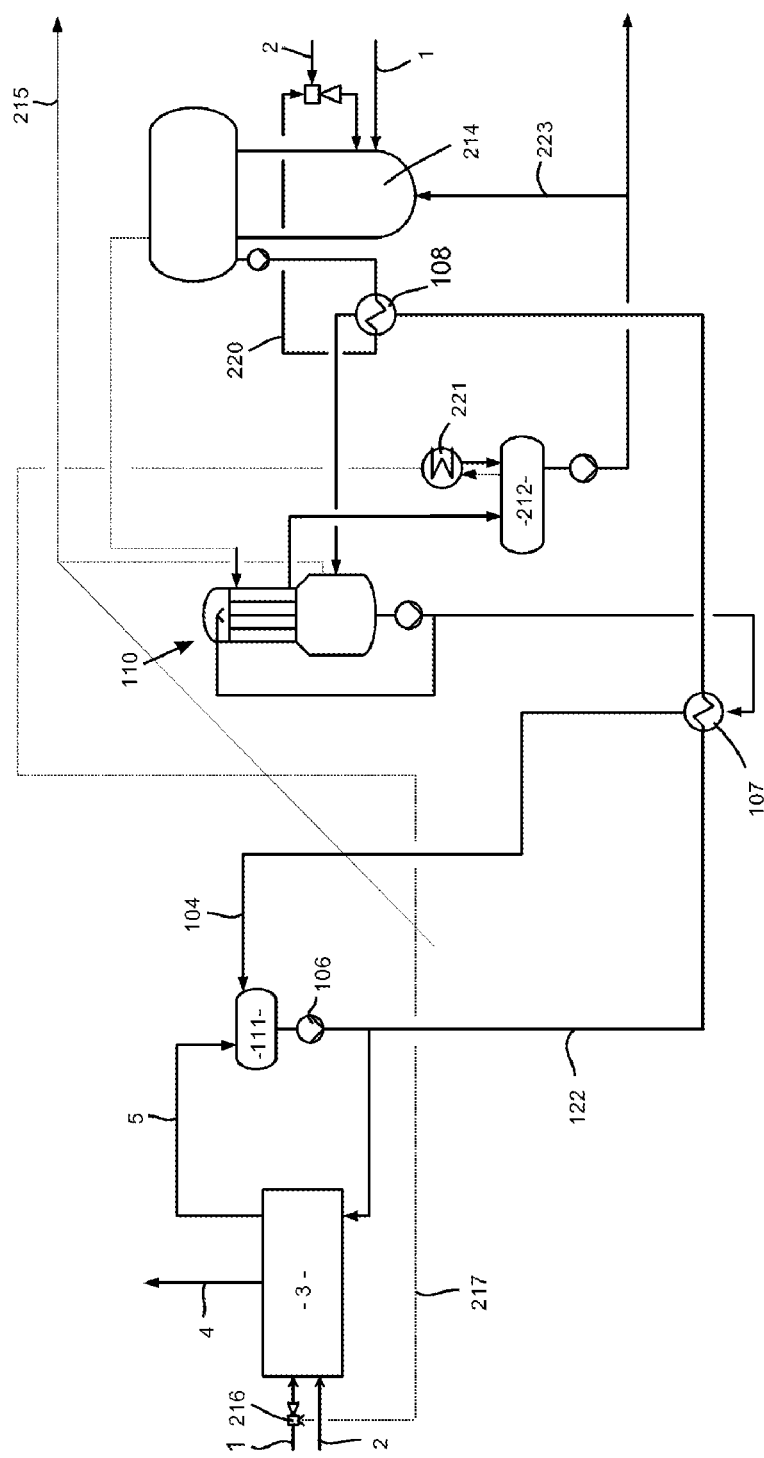
FIG. 3 shows in a schematic depiction a second exemplary embodiment of a device as provided by the invention for synthesizing 1,2-dichloroethane from ethylene and chlorine.

FIG. 3 depicts a second exemplary embodiment of a device for synthesizing 1,2-dichloroethane according to the invention. In this exemplary embodiment, the vaporizing step is heated with reaction heat coupled out of an HTDC plant.

The HTDC plant depicted by way of example in FIG. 3 was already described in EP 1 161 406. However, other HTDC processes are also suitable for heating the vaporizing step of the present invention.

Ethylene 1 and chlorine 2 are fed into an LTDC reactor 3, where they react to form EDC. The reactor off-gas stream 4 is withdrawable at the top of the reactor 3. The LTDC reactor 3 has withdrawn from it a liquid, catalyst-containing EDC stream 5, which is passed into a receiver 111. In a preferred embodiment, the EDC stream 5 is greater than the EDC quantity produced in the LTDC reactor 3. The receiver 111 has withdrawn from it, by means of a pump 106, an EDC stream 122 which, in a preferred embodiment of the invention, is greater than the EDC quantity produced in the LTDC reactor 3. The EDC stream 122 is passed through one or more heat exchangers 107, 108 which serve to preheat the stream and are heated with the EDC stream 104 from the bottom end of the vaporizing apparatus 110 and/or with a liquid, hot EDC stream 220 from the HTDC plant. After preheating, the EDC stream 122 enters the vaporizing apparatus 110, where an EDC quantity corresponding to the EDC quantity produced in the LTDC reactor 3 is vaporized. The vaporized LTDC product stream 215 may for example be fed in vapor form into a distillation column or, in a further preferred (non-depicted) embodiment of the invention, used to preheat, by condensation, the liquid EDC from the LTDC reactor 3.

The nonvaporized fraction of the EDC from the vaporizing apparatus 110 is cooled down by heat exchange with the stream 122 from the receiver 111 and conveyed back into the receiver 111. The EDC partly condensed in the vaporizing apparatus 110 is collected in the HTDC product receiver 212 and pumped as product 213 to the plant limits and/or as backstream 223 back to the HTDC reactor 214. Downstream of the product receiver 212 is an off-gas condensation sector 221, which also may contain a freezer (not depicted). The off-gas from the HTDC reactor 214, which contains ethylene in addition to other noncondensable constituents, is compressed in a gas jet gas compressor 216 by means of the ethylene feed stream 1 to the LTDC reactor 3 and fed into the LTDC reactor 3.

The method described in the second exemplary embodiment is particularly useful for upgrading existing LTDC plants when the capacity is to be increased at the same time as the LTDC plant upgrade by installing an additional HTDC plant.

In the above-described devices and methods for synthesizing 1,2-dichloroethane from ethylene and chlorine by low temperature direct chlorination of ethylene in the presence of a catalyst in a reactor 3 under conditions where the synthesized 1,2-dichloroethane condenses out, while the ethylene and the chlorine are gaseous, the stoichiometric ratio of ethylene to chlorine in the reactor 3 is adjusted such that ethylene is present in excess. This reduces the purification requirements of the synthesized 1,2-dichloroethane and substantially extends the useful life of reactor 3.

LIST OF REFERENCE SIGNS

1 ethylene
2 chlorine
3 LTDC reactor
4 LTDC reactor off-gas
5 product EDC from reactor
6 EDC wash
7 wash water
8 aqueous sodium hydroxide solution
9 EDC, dry
10 wastewater stream
11 product EDC, water-containing
12 dewatering column
13 high boilers column
14 EDC product stream, purified
15 vacuum column
16 water and low boilers
17 product EDC, purified
18 EDC, moist, from oxychlorination
19 back EDC from EDC cracking
20 EDC+high boilers
21 back EDC from vacuum column
22 high boilers
23 column off-gas
104 EDC backstream to circuit receiver
106 circuit pump
107 preheater
108 preheater
109 product condenser
110 falling stream evaporator
111 circuit receiver
112 product receiver
113 return stream container
114 high boilers column
115 vapor stream
116 back EDC from EDC cracking
117 dried EDC from oxychlorination
118 EDC backstream to LTDC reactor
119 LTDC reactor off-gas
120 EDC from evaporator
121 condensed EDC from evaporator
122 EDC to evaporator
212 HTDC product receiver
213 HTDC product
214 HTDC reactor
215 LTDC product stream
216 gas jet gas compressor
217 HTDC reactor off-gas
220 EDC circulation stream, HTDC
221 HTDC postcondenser
223 EDC to HTDC reactor

What is claimed is:

1. A method for synthesizing 1,2-dichloroethane from ethylene and chlorine by low temperature direct chlorination of ethylene in the presence of a catalyst in a reactor under conditions where the synthesized 1,2-dichloroethane condenses out while the ethylene and the chlorine are gaseous, which method comprises the step of adjusting the stoichiometric ratio of ethylene to chlorine in the reactor such that ethylene is present in excess.

2. The method as claimed in claim 1, wherein the stoichiometric ratio of ethylene to chlorine is not less than 1.01:1.

3. The method as claimed in claim 1, wherein the stoichiometric ratio of ethylene to chlorine in the reactor is monitored and the feed of ethylene and chlorine to the reactor is closed loop controlled such that ethylene is present in excess.

4. The method as claimed in claim 1, wherein a 1,2-dichloroethane liquid stream is withdrawn from the reactor and is partly vaporized in a vaporizing device.

5. The method as claimed in claim 4, wherein less than 50% of the 1,2-dichloroethane stream removed from the reactor is vaporized in the vaporizing device.

6. The method as claimed in claim 4, wherein the proportion to which the 1,2-dichloroethane stream removed from the reactor is vaporized in the vaporizing device corresponds to the 1,2-dichloroethane quantity produced in said reactor.

7. The method as claimed in claim 4, wherein the vaporizing device is configured as a falling stream evaporator.

8. The method as claimed in claim 4, wherein the non-vaporized proportion of the 1,2-dichloroethane stream withdrawn from the reactor is returned into the reactor.

9. The method as claimed in claim 4, wherein the vaporizing device is heated using the reaction heat from a plant for high temperature direct chlorination of ethylene.

10. The method as claimed in claim 4, wherein the vaporous 1,2-dichloroethane stream emerging from the vaporizing device is fed into a distillation column.

11. The method as claimed in claim 4, wherein the vaporizing device is heated using the condensation heat from the vapor of a distillation column.

12. The method as claimed in claim 10, wherein the distillation column is used to separate off compounds having a higher boiling point than 1,2-dichloroethane.

13. The method as claimed in claim 11, wherein the distillation column is operated at an overhead temperature in the range from 120° C. to 150° C.

14. The method as claimed in claim 4, wherein before being fed to the vaporizing device, the 1,2-dichloroethane stream removed from the reactor is preheated using a 1,2-dichloroethane stream withdrawn from the vaporizing device and/or using a 1,2-dichloroethane stream from a plant for high temperature direct chlorination of ethylene.

15. The method as claimed in claim 1, wherein the catalyst comprises $FeCl_3$ and/or NaCl.

16. The method as claimed in claim 1, wherein an ethylene-containing off-gas from a high temperature direct chlorination reactor is fed to the reactor.

17. A device for synthesizing 1,2-dichloroethane from ethylene and chlorine according to the method of claim 1, wherein the device is configured for low temperature direct chlorination of ethylene in the presence of a catalyst in a reactor under conditions where the synthesized 1,2-dichloroethane condenses out while the ethylene and the chlorine are gaseous, wherein the stoichiometric ratio of ethylene to chlorine in the reactor is adjustable such that ethylene is present in excess.

18. The method as claimed in claim 4, wherein the vaporizing device is single-staged.

19. The method as claimed in claim 13, wherein the overhead temperature is in the range from 127° C. to 135° C.

20. The method as claimed in claim 14, wherein the 1,2-dichloroethane stream is liquid.

\* \* \* \* \*